(12) United States Patent
Porath et al.

(10) Patent No.: US 6,957,101 B2
(45) Date of Patent: Oct. 18, 2005

(54) TRANSIENT EVENT MAPPING IN THE HEART

(76) Inventors: Joshua Porath, 18 Kidron Street, Haifa (IL) 34463; Jonathan Lessick, 9, Martin Bover Street, Haifa (IL) 34861

(*) Notice: Subject to any disclaimer, the term of this patent is extended or adjusted under 35 U.S.C. 154(b) by 11 days.

(21) Appl. No.: 10/644,533

(22) Filed: Aug. 20, 2003

(65) Prior Publication Data

US 2004/0039293 A1 Feb. 26, 2004

Related U.S. Application Data

(60) Provisional application No. 60/404,883, filed on Aug. 21, 2002.

(51) Int. Cl.[7] .............................................. A61B 5/04
(52) U.S. Cl. ..................................................... 600/523
(58) Field of Search ................................ 600/509, 518, 600/519, 523, 525, 407

(56) References Cited

U.S. PATENT DOCUMENTS

| | | | |
|---|---|---|---|
| 4,414,981 A | * | 11/1983 | Wong et al. ................. 600/525 |
| 4,649,924 A | | 3/1987 | Taccardi |
| 5,297,549 A | | 3/1994 | Beatty et al. |
| 5,311,866 A | | 5/1994 | Kagan et al. |
| 5,385,146 A | | 1/1995 | Goldreyer |
| 5,391,199 A | | 2/1995 | Ben-Haim |
| 5,450,846 A | | 9/1995 | Goldreyer |
| 5,471,982 A | | 12/1995 | Edwards et al. |
| 5,487,391 A | | 1/1996 | Panescu |
| 5,546,951 A | | 8/1996 | Ben-Haim |
| 5,662,108 A | | 9/1997 | Budd et al. |
| 5,718,241 A | | 2/1998 | Ben-Haim et al. |
| 5,738,096 A | | 4/1998 | Ben-Haim |
| 5,769,846 A | | 6/1998 | Edwards et al. |
| 5,848,972 A | | 12/1998 | Triedman et al. |
| 5,897,529 A | | 4/1999 | Ponzi |
| 5,904,651 A | | 5/1999 | Swanson et al. |
| 5,938,603 A | | 8/1999 | Ponzi |
| 5,964,757 A | | 10/1999 | Ponzi |
| 6,004,269 A | | 12/1999 | Crowley et al. |
| 6,052,618 A | | 4/2000 | Dahlke et al. |
| 6,066,094 A | | 5/2000 | Ben-Haim |

(Continued)

FOREIGN PATENT DOCUMENTS

| | | |
|---|---|---|
| EP | 0776176 B1 | 4/1997 |
| EP | 1125549 A2 | 8/2001 |
| EP | 1166714 A1 | 1/2002 |
| EP | 1508300 A1 | 2/2005 |
| WO | WO 94/06349 A1 | 3/1994 |
| WO | WO 97/24981 A2 | 7/1997 |
| WO | WO 99/06112 A1 | 2/1999 |

OTHER PUBLICATIONS

U.S. Appl. No. 09/506,766, pending, Biosense, Inc.
European Search Report EP 04254991 dated Jan. 12, 2005.

*Primary Examiner*—George Manuel

(57) ABSTRACT

A method for performing a medical procedure is provided, including recording geometric information at a plurality of time points in a plurality of cardiac cycles of a heart of a subject. Subsequently, a transient event is detected that is produced at a location on the heart during a cardiac cycle. A time of occurrence of the transient event is identified in the cardiac cycle during which the transient event occurred. A map of the heart is displayed responsive to the identified time of occurrence and the geometric information recorded at a time point in the cardiac cycle that corresponds to the time of occurrence of the transient event.

1 Claim, 3 Drawing Sheets

U.S. PATENT DOCUMENTS

| | | |
|---|---|---|
| 6,216,027 B1 | 4/2001 | Willis et al. |
| 6,226,542 B1 * | 5/2001 | Reisfeld ................. 600/407 |
| 6,285,898 B1 | 9/2001 | Ben-Haim |
| 6,301,496 B1 | 10/2001 | Reisfeld |
| 6,353,751 B1 | 3/2002 | Swanson et al. |
| 6,368,285 B1 | 4/2002 | Osadchy et al. |
| 6,385,476 B1 | 5/2002 | Osadchy et al. |
| 6,892,091 B1 * | 5/2005 | Ben-Haim et al. .......... 600/509 |
| 2004/0039293 A1 | 2/2004 | Porath et al. |

* cited by examiner

TRANSIENT EVENT MAPPING IN THE HEART

CROSS-REFERENCES TO RELATED APPLICATIONS

This application is a non-provisional patent application of U.S. provisional patent application No. 60/404,883 filed on Aug. 21, 2002 entitled, "TRANSIENT EVENT MAPPING IN THE HEART," which is assigned to the assignee of the present patent application and is incorporated herein by reference.

FIELD OF THE INVENTION

The present invention relates generally to invasive methods for geometric and electrical mapping of the heart, and specifically to methods for analyzing a transient event of the heart.

BACKGROUND OF THE INVENTION

Cardiac mapping is used to locate aberrant electrical pathways and currents within the heart, as well as to diagnose mechanical and other aspects of cardiac activity. Various methods and devices have been described for mapping the heart.

U.S. Pat. Nos. 5,546,951 and 6,066,094 to Ben-Haim, and European Patent 0 776 176 to Ben-Haim et al., which are assigned to the assignee of the present patent application and are incorporated herein by reference, disclose methods for sensing an electrical property of heart tissue, for example, local activation time, as a function of the precise location within the heart. The data are acquired with a catheter that has electrical and location sensors in its distal tip, and which is advanced into the heart. Techniques for sensing cardiac electrical activity are also described in U.S. Pat. No. 5,471,982 to Edwards et al., commonly-assigned U.S. Pat. Nos. 5,391,199 and 6,066,094 to Ben-Haim, U.S. Pat. No. 6,052,618 to Dahlke et al., and in PCT patent publications WO94/06349 and WO97/24981, which are incorporated herein by reference.

Methods of creating a map of the electrical activity of the heart based on these data are disclosed in U.S. Pat. Nos. 6,226,542 and 6,301,496 to Reisfeld, which are assigned to the assignee of the present patent application and are incorporated herein by reference. As indicated in these patents, location and electrical activity is preferably initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, which alters the propagation of the heart's electrical activity and restores normal heart rhythm. Methods for constructing a cardiac map of the heart are also disclosed in U.S. Pat. Nos. 5,391,199 and 6,285,898 to Ben-Haim, and in U.S. Pat. Nos. 6,368,285 and 6,385,476 to Osadchy et al., which are assigned to the assignee of the present patent application and are incorporated herein by reference.

Catheters containing position sensors may be used to determine the trajectory of points on the cardiac surface. These trajectories may be used to infer motion characteristics such as the contractibility of the tissue. As disclosed in U.S. Pat. No. 5,738,096 to Ben-Haim, which is assigned to the assignee of the present application and which is incorporated herein by reference, maps depicting such motion characteristics may be constructed when the trajectory information is sampled at a sufficient number of points in the heart.

In order to speed up the process of data acquisition in the heart, multiple-electrode catheters have been developed to simultaneously measure electrical activity at multiple points in the heart chamber. U.S. Pat. No. 5,487,391 to Panescu, which is incorporated herein by reference, is directed to systems and methods for deriving and displaying the propagation velocities of electrical events in the heart and is illustrative of some contact methods found in the art. In the system disclosed in the '391 patent, the electrical probe is a three-dimensional structure that takes the form of a basket. In the illustrated embodiment, the basket is composed of 8 splines, each of which carries eight electrodes, for a total of 64 electrodes in the probe. The basket structure is designed such that when deployed, its electrodes are held in intimate contact against the endocardial surface.

European Patent Application EP 1 125 549 and corresponding U.S. patent application Ser. No. 09/506,766 to Ben-Haim et al., which are assigned to the assignee of the present patent application and are incorporated herein by reference, describe techniques for rapidly generating an electrical map of a chamber of the heart. The catheter used for these techniques is described as comprising a contact electrode at the distal tip of the catheter and an array of non-contact electrodes on the shaft of the catheter near the distal end. The catheter also comprises at least one position sensor. Information from the non-contact electrodes and contact electrode is used for generating a geometric and electrical map of the cardiac chamber.

U.S. Pat. No. 5,848,972 to Triedman et al., which is incorporated herein by reference, describes a method for endocardial activation mapping using a multi-electrode catheter. A multi-electrode catheter is advanced into a chamber of the heart. Anteroposterior (AP) and lateral fluorograms are obtained to establish the position and orientation of each of the electrodes. Electrograms are recorded from each of the electrodes in contact with the cardiac surface relative to a temporal reference such as the onset of the P-wave in sinus rhythm from a body surface ECG. After the initial electrograms are recorded, the catheter is repositioned, and fluorograms and electrograms are once again recorded. An electrical map is then constructed from the above information.

U.S. Pat. No. 4,649,924 to Taccardi, which is incorporated herein by reference, describes a method for the detection of intracardiac electrical potential fields. The '924 patent is illustrative of non-contact methods that have been proposed to simultaneously acquire a large amount of cardiac electrical information. In the method of the '924 patent, a catheter having a distal end portion is provided with a series of sensor electrodes distributed over its surface and connected to insulated electrical conductors for connection to signal sensing and processing means. The size and shape of the end portion are such that the electrodes are spaced substantially away from the wall of the cardiac chamber. The method of the '924 patent is said to detect the intracardiac potential fields in only a single cardiac beat. The sensor electrodes are preferably distributed on a series of circumferences lying in planes spaced from each other. These planes are perpendicular to the major axis of the end portion of the catheter. At least two additional electrodes are provided adjacent the ends of the major axis of the end portion. The '924 patent describes a single exemplary embodiment in which the catheter comprises four circumferences with eight electrodes spaced equiangularly on each circumference. Thus, in that exemplary embodiment, the catheter comprises at least 34 electrodes (32 circumferential and 2 end electrodes).

PCT application WO 99/06112 to Rudy, which is incorporated herein by reference, describes an electrophysiological cardiac mapping system and method based on a non-contact, non-expanded multi-electrode catheter. Electrograms are obtained with catheters having from 42 to 122 electrodes. The relative geometry of the probe and the endocardium must be obtained via an independent imaging modality such as transesophageal echocardiography. After the independent imaging, non-contact electrodes are used to measure cardiac surface potentials and construct maps therefrom.

U.S. Pat. No. 5,297,549 to Beatty et al., which is incorporated herein by reference, describes a method and apparatus for mapping the electrical potential distribution of a heart chamber. An intra-cardiac multielectrode mapping catheter assembly is inserted into the heart. The mapping catheter assembly includes a multi-electrode array with an integral reference electrode, or, preferably, a companion reference catheter. In use, the electrodes are deployed in the form of a substantially spherical array. The electrode array is spatially referenced to a point on the endocardial surface by the reference electrode or by the reference catheter, which is brought into contact with the endocardial surface. Knowledge of the location of each of the electrode sites on the array, as well as a knowledge of the cardiac geometry is determined by impedance plethysmography.

U.S. Pat. No. 5,311,866 to Kagan et al., which is incorporated herein by reference, describes a heart mapping catheter assembly including an electrode array defining a number of electrode sites. The mapping catheter assembly has a lumen to accept a reference catheter having a distal tip electrode assembly which may be used to probe the heart wall. In the preferred construction, the mapping catheter includes a braid of insulated wires, preferably having 24 to 64 wires in the braid, each of which are used to form electrode sites. The catheter is said to be readily positionable in the heart to be used to acquire electrical activity information from a first set of non-contact electrode sites and/or a second set of in-contact electrode sites.

U.S. Pat. Nos. 5,385,146 and 5,450,846 to Goldreyer, which are incorporated herein by reference, describe a catheter that is said to be useful for mapping electrophysiological activity within the heart. The catheter body has a distal tip which is adapted for delivery of a stimulating pulse for pacing the heart or for ablating tissue in contact with the tip. The catheter further comprises at least one pair of orthogonal electrodes to generate a difference signal indicative of the local cardiac electrical activity adjacent the orthogonal electrodes.

U.S. Pat. No. 5,662,108 to Budd et al., which is incorporated herein by reference, describes a process for measuring electrophysiological data in a heart chamber. The method involves, in part, positioning a set of active and passive electrodes in the heart; supplying current to the active electrodes, thereby generating an electric field in the heart chamber; and measuring this electric field at the passive electrode sites. In one of the described embodiments, the passive electrodes are contained in an array positioned on an inflatable balloon of a balloon catheter.

U.S. Pat. No. 5,718,241 to Ben-Haim, U.S. Pat. No. 6,216,027 to Willis et al., U.S. Pat. No. 6,004,269 to Crowley at al., and U.S. Pat. No. 5,769,846 to Edwards et al., which are incorporated herein by reference, describe techniques for directing a catheter to a desired treatment site in the heart and ablating tissue at the site. U.S. Pat. No. 6,353,751 to Swanson et al., which is incorporated herein by reference, describes systems for guiding a movable electrode within an array of electrodes located within the body. U.S. Pat. No. 5,904,651 to Swanson et al., which is incorporated herein by reference, describes a catheter tube with an imaging element and a support structure for stabilizing the imaging element. U.S. Pat. Nos. 5,964,757, 5,897,529, and 5,938,603 to Ponzi, which are incorporated herein by reference, describe a steerable catheter having a control handle.

SUMMARY OF THE INVENTION

It is an object of some aspects of the present invention to provide improved apparatus and methods for geometric and electrical mapping of the heart.

It is also an object of some aspects of the present invention to provide improved apparatus and methods for treatment of transient cardiac events, such as ectopic heartbeats.

It is a further object of some aspects of the present invention to provide improved apparatus and methods that increase the accuracy of procedures for cardiac tissue ablation for treatment of transient cardiac events.

It is yet a further object of some aspects of the present invention to provide apparatus and methods that increase the effectiveness of procedures for cardiac tissue ablation for treatment of transient cardiac events.

In preferred embodiments of the present invention, a mapping probe, preferably a catheter comprising position sensors and electrodes, is inserted into a chamber of the heart, and is used to acquire and record geometric information about the chamber, typically over an entire cardiac cycle that includes an annotation point in the cycle, such as end-diastole. A geometric map of the chamber at the annotation point is generated and displayed, after which the catheter is positioned near the site of an expected transient event on the wall of the chamber. If a transient event occurs, a determination is made of the point in the cardiac cycle, relative to the most recent annotation point, at which the transient event commenced. A map is generated at the point in the cycle recorded at or immediately prior to the determined point in the cycle at which the transient event commenced. This map is typically generated based on geometric data taken in the seconds or minutes leading up to the transient event. Using the map so generated, data generated by the electrode (or electrodes) nearest to the site of the transient event are used to generate information about the site of the transient event, which information can be used for diagnosis and/or treatment, such as ablation of the defective tissue.

Typically, embodiments of the present invention in effect enable the mapping of a chamber of the heart during a single transient event, such as an ectopic heartbeat. Using standard techniques, a plurality of contact points between the catheter and the wall of the chamber, typically more than five, would typically be needed at any given reference point in the cardiac cycle for which a map of satisfactory quality is to be generated. Therefore, since only one or at most a few transient events can be expected to occur during a catheterization procedure, it would not appear to be feasible, without using the techniques of these embodiments of the present invention, to generate a map of satisfactory quality of the chamber at the point in the cardiac cycle at which the transient event occurs. A possible alternative approach, the use of a map generated at a previously-determined reference point, would not appear to provide a useful solution to the problem because the shape of the chamber during the transient event is typically very different from the shape of the chamber derived at the reference point. Typically, the transient event map, generated using the techniques described herein, facilitates a return to the site of the transient event in order to perform further diagnosis or therapy on essentially the precise location of the defective tissue causing transient events.

In preferred embodiments of the present invention, the catheter comprises an array of shaft electrodes on its outer surface. The electrodes are preferably attached to the catheter in a manner similar to one of the arrangements described in the above-cited European Patent Application EP 1 125 549 and corresponding U.S. patent application Ser. No. 09/506,766 to Ben-Haim et al. Alternatively, the shaft electrodes comprise ring electrodes, or substantially any other suitable type of surface electrodes, as are known in the art. Additionally, the catheter preferably has at least one tip electrode, typically at or near a distal tip of the catheter. The tip electrode is also useful for sending electrical signals to the heart for diagnostic purposes, e.g., for pace mapping, and/or for therapeutic purposes, e.g., for ablating defective cardiac tissues.

The catheter further comprises at least one position sensor that generates or receives signals used to determine the position and orientation of the catheter within the heart. This position sensor is preferably affixed adjacent to the distal tip of the catheter. There is preferably a fixed positional and orientational relationship of the position sensor, the distal tip, and the tip electrode. The catheter typically further comprises at least one additional position sensor, preferably affixed near a proximal end of the array of shaft electrodes. Suitable position sensors are described, for example, in the above-cited U.S. Pat. No. 5,391,199 to Ben-Haim, the above-cited European Patent 0 776 176 to Ben-Haim et al., co-pending U.S. patent application Ser. No. 10/029,473, filed Dec. 21, 2001, entitled, "Wireless position sensor," and/or in co-pending U.S. patent application Ser. No. 10/029,595, also filed Dec. 21, 2001, entitled, "Implantable and insertable tags," which are assigned to the assignee of the present patent application and are incorporated herein by reference.

In preferred embodiments of the present invention, the catheter is coupled to a console, which enables a user to observe and regulate the functions of the catheter. The console includes a processor, preferably a computer with appropriate signal processing circuits that are typically contained inside a housing of the computer. The processor is coupled to a display. The signal processing circuits typically receive, amplify, filter and digitize signals from the catheter, including signals generated by the position sensors and the electrodes. The digitized signals are received and used by the console to compute the location and orientation of the catheter and to analyze the electrical signals from the electrodes.

Preferably, the position information at each time point in the cardiac cycle is acquired, and a geometric map based thereupon is generated when needed, e.g., using techniques described in the above-cited U.S. Pat. Nos. 6,226,542 and 6,301,496 to Reisfeld, European patent application EP 1 125 549 and corresponding U.S. patent application Ser. No. 09/506,766 to Ben-Haim et al., and/or co-pending U.S. patent application Ser. No. 09/598,862 to Govari, which are incorporated herein by reference, adapted for use with the techniques described herein. Preferably, but not necessarily, electrical signals from the electrodes are measured when appropriate using techniques described in copending U.S. patent application Ser. No. 09/805,093, filed Mar. 13, 2001, entitled, "Apparatus and method for measuring a plurality of electrical signals from the body of a patient," which is assigned to the assignee of the present patent application and which is incorporated herein by reference.

In some preferred embodiments of the present invention, in order to generate additional information regarding the site of a recorded transient event, the catheter is repositioned near the site of the transient event, preferably at a different orientation compared to its orientation during recording of the transient event. If the transient event reoccurs, additional information regarding the site of the transient event is generated, using the procedures described above.

In some preferred embodiments of the present invention, after the initial data collection has been completed and the location of the site of the transient event has been determined, a map is displayed of the chamber reflecting the point in time in the cardiac cycle at which the transient event occurred. Using this map, the tip of the catheter is positioned at the site of the transient event. For some applications, a therapeutic or diagnostic procedure is performed by the catheter while the map is displayed representing the shape of the chamber immediately before the transient event.

Optionally, instead of performing the procedure while that map is shown, the tip is physically held on the site of the transient event on the wall of the chamber at least through the next occurrence of the annotation point in the cardiac cycle, at which point position information for the tip is acquired. Using this position information, the location of the transient event on the map of the wall at the annotation point in the cardiac cycle is determined. Preferably, with this absolute knowledge of the site of the transient event in the reference frame of the annotation point, diagnosis, additional data collection, and/or treatment (for example, ablation) is performed. Similarly, the catheter can be removed from the site and subsequently brought back to the site, facilitated by, for example, a marker representing the site being displayed on a map showing the heart at the annotation point.

The present invention will be more fully understood from the following detailed description of the preferred embodiments thereof, taken together with the drawings in which:

DETAILED DESCRIPTION OF PREFERRED EMBODIMENTS

Figure 1:
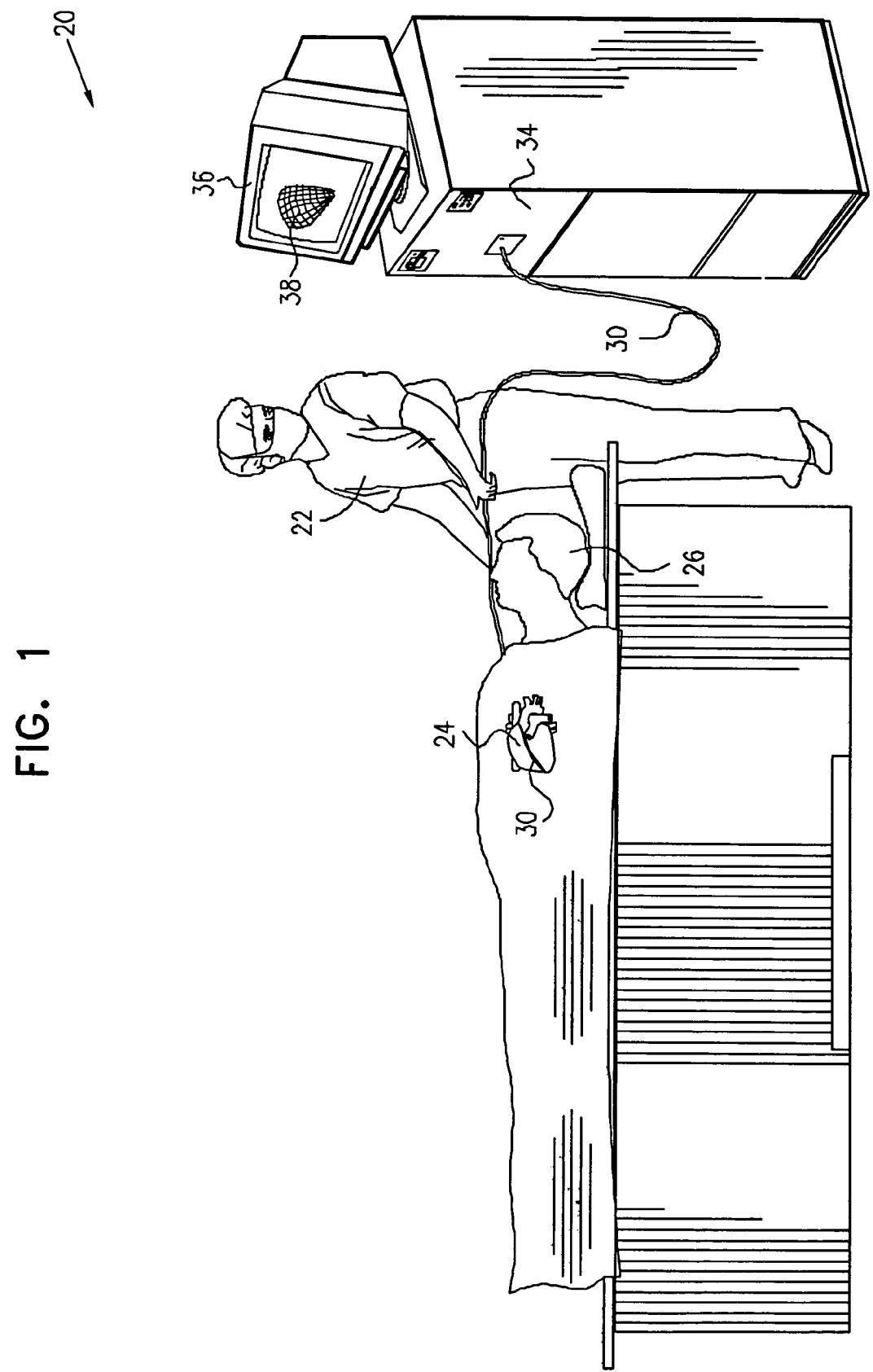
FIG. 1 is a schematic, pictorial illustration of a system for mapping transient events in the heart, in accordance with a preferred embodiment of the present invention.

FIG. 1 is a schematic, pictorial illustration of a mapping system 20, for mapping of electrical activity in a heart 24 of a subject 26, in accordance with a preferred embodiment of the present invention. System 20 comprises an elongated probe, preferably a catheter 30, which is inserted by a user 22 through a vein or artery of the subject into a chamber of the heart.

Figure 2:
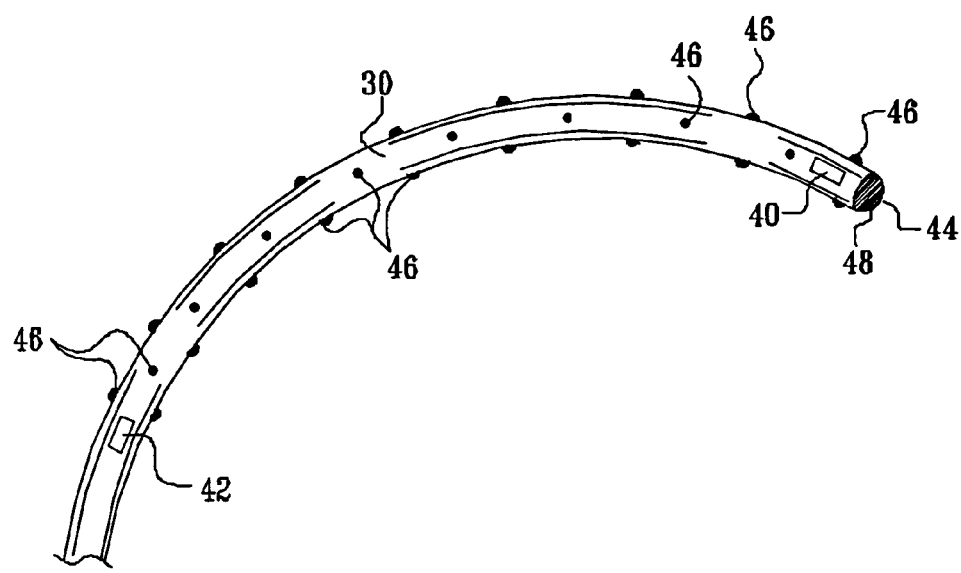
FIG. 2 is a schematic, pictorial illustration of a distal portion of a catheter used in the system of FIG. 1, in accordance with a preferred embodiment of the present invention.

FIG. 2 is a schematic, pictorial illustration showing a distal portion of catheter 30, which is inserted into heart 24. The catheter preferably comprises an array of shaft electrodes 46 on its outer surface. Electrodes 46 are preferably attached to catheter 30 in one of the arrangements described in the above-cited European Patent Application EP 1 125 549 and corresponding U.S. patent application Ser. No. 09/506,766 to Ben-Haim et al. Alternatively, the shaft electrodes may comprise ring electrodes, or substantially any other suitable type of surface electrodes, as are known in the art. Additionally, the catheter preferably has at least one tip electrode 48, typically at or near a distal tip 44 of the catheter, as described, for example, in the '766 application. Tip electrode 48 is also useful for sending electrical signals to the heart for diagnostic purposes, e.g., for pace mapping, and/or for therapeutic purposes, e.g., for ablating defective cardiac tissues.

Catheter 30 further comprises at least one position sensor 40 that generates or receives signals used to determine the position and orientation of catheter 30 within the heart. Position sensor 40 is preferably affixed adjacent to distal tip 44. There is preferably a fixed positional and orientational relationship of position sensor 40, distal tip 44 and tip electrode 48. Catheter 30 typically further comprises at least one additional position sensor 42, preferably affixed near a proximal end of the array of shaft electrodes 46. Suitable position sensors are described, for example, in the above-cited U.S. Pat. No. 5,391,199 to Ben-Haim, the above-cited European Patent 0 776 176 to Ben-Haim et al., co-pending U.S. patent application Ser. No. 10/029,473, filed Dec. 21, 2001, entitled, "Wireless position sensor," and/or in co-pending U.S. patent application Ser. No. 10/029,595, also filed Dec. 21, 2001, entitled, "Implantable and insertable tags," which are assigned to the assignee of the present patent application and are incorporated herein by reference. A preferred electromagnetic mapping sensor is manufactured by Biosense Webster (Israel) Ltd., (Tirat Hacarmel, Israel) and marketed under the trade designation NOGA™. Alternatively or additionally, substantially any other suitable type of position/coordinate sensing device known in the art is used for position sensing. Still further alternatively or additionally, catheter 30 is marked with one or more markers whose positions can be determined from outside of the body, such as radio-opaque markers to facilitate fluoroscopic measurements. "Position" information, as used in the context of the present patent application and in the claims, is to be understood as being indicative of the combination of location and orientation information, unless the context clearly indicates otherwise.

Preferably, position sensing techniques are used that achieve continuous generation of six dimensions of location and orientation information with respect to each of sensors 40 and 42. Alternatively, position sensing techniques are used that achieve only three dimensions of location and two dimensions of orientation information. In this case, the third dimension of orientation (typically rotation of catheter 30 about its longitudinal axis) can be inferred if needed from a comparison of the coordinates of the two sensors and from mechanical information.

Catheter 30 is coupled to a console 34 (FIG. 1), which enables user 22 to observe and regulate the functions of the catheter. Console 34 includes a computer, which includes a memory a processor, and appropriate signal processing circuits. The processor is coupled to a display 36. The signal processing circuits typically receive, amplify, filter and digitize signals from catheter 30, including signals generated by position sensors 40 and 42 and electrodes 46 and 48. The digitized signals are received and used by the console to compute the location and orientation of catheter 30 and to analyze the electrical signals from the electrodes. The information derived from this analysis is used as described hereinbelow, in order to generate a geometric and/or electrical map 38 of heart 24.

Typically, system 20 includes other elements, which are not shown in the figures for the sake of simplicity. Some of these elements are described in the above-cited U.S. Pat. Nos. 6,226,542 and 6,301,496 to Reisfeld. For example, system 20 preferably includes an ECG monitor, coupled to receive signals from one or more body surface electrodes, so as to provide an ECG synchronization signal to console 34. The system preferably also includes field generators located external to subject 26 for generating fields used in position sensing. For some applications, a reference position sensor, typically either on an externally-applied reference patch attached to the exterior of the patient's body, or on an internally-placed catheter, is inserted into heart 24 and maintained in a fixed position relative to the heart. By comparing the position of catheter 30 to that of the reference catheter, the coordinates of catheter 30 are accurately determined relative to the heart, irrespective of the patient's motion. Alternatively, any other suitable method may be used to compensate for such motion.

Figure 3A:
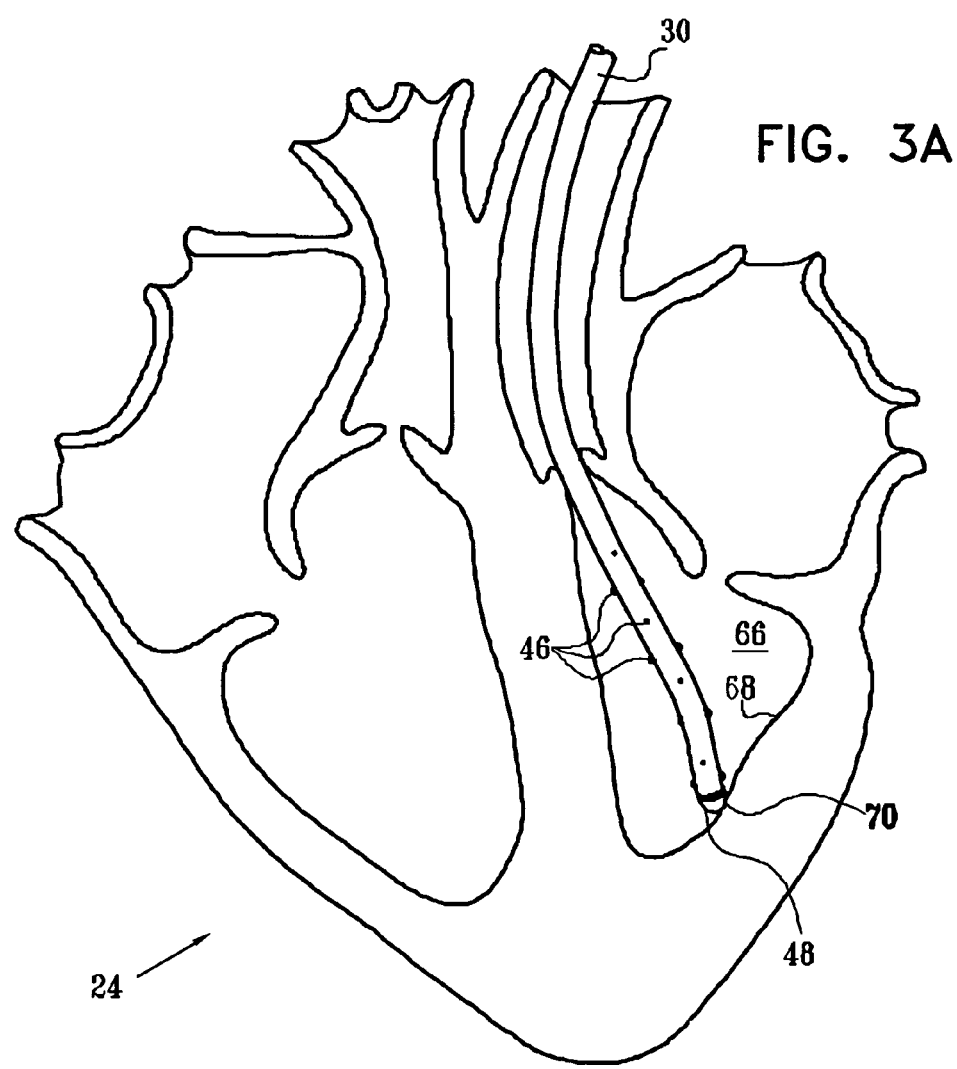
FIGS. 3A and 3B are schematic, sectional illustrations of a heart into which the distal end of the catheter of FIG. 2 has been inserted, in accordance with a preferred embodiment of the present invention.
Figure 3B:
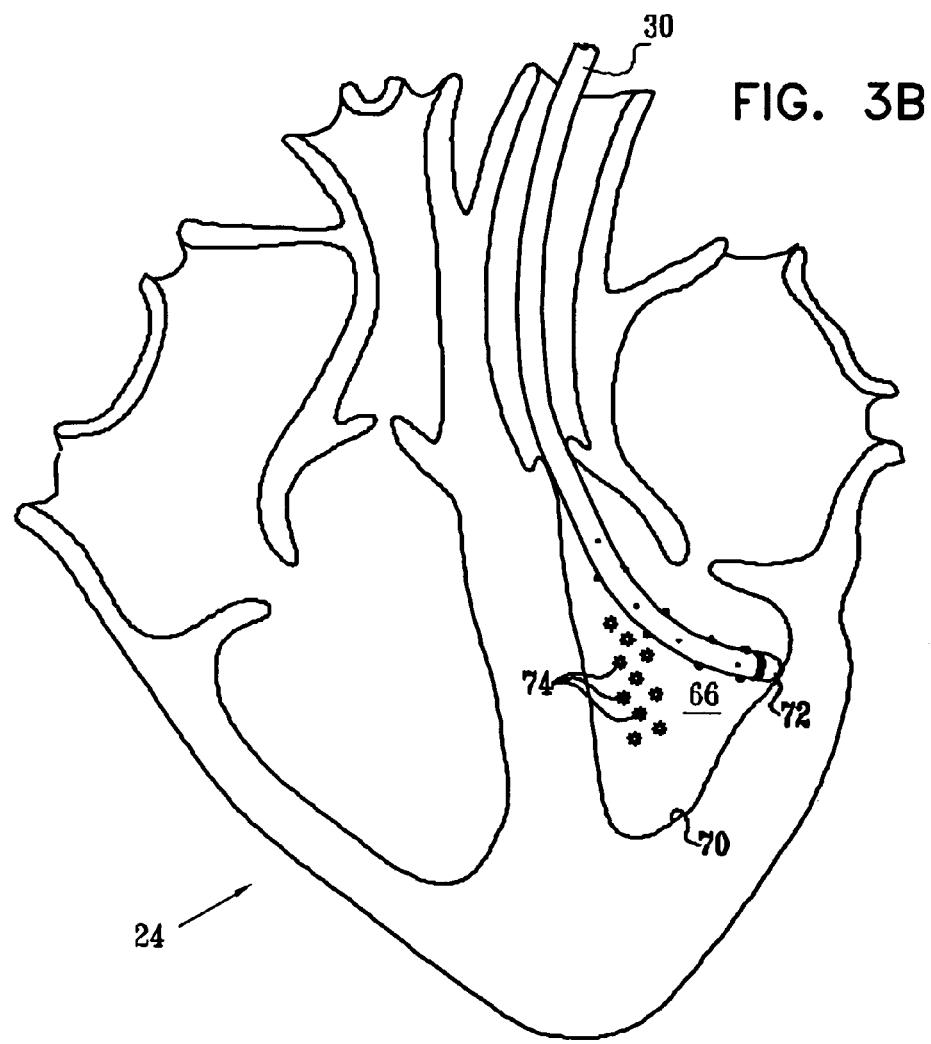

Reference is now made to FIGS. 3A and 3B, which are schematic, sectional illustrations of heart 24, showing the distal portion of catheter 30 inserted through the aorta into the heart, in accordance with a preferred embodiment of the present invention. For clarity of illustration, the figures and the descriptions herein refer to simplified, two-dimensional examples. The extension of the principles illustrated herein to three-dimensional mapping and positioning will be clear to those skilled in the art. Catheter 30 is advanced into a chamber 66 of the heart, such as the left ventricle, preferably in a vicinity of a site suspected of initiating a transient event, such as an ectopic heartbeat. It will be appreciated that other chambers can be accessed using techniques known in the art, and that access to any of the chambers can be attained via the venous circulation, as well.

Position information for chamber 66 is acquired for substantially the entire cardiac cycle by acquiring information at frequent intervals, for example, at 10 millisecond intervals. Information is acquired by placing catheter 30 in a plurality of positions in the chamber, as described hereinbelow. The information is stored in the memory of console 34 in bins representing each sequential time interval in the cardiac cycle. Typically, intervals of 10 ms are utilized, although it is to be appreciated that other intervals are also suitable. Preferably, an annotation time point P in the cardiac cycle, such as end-diastole, is used to define time t=0 in the cardiac cycle, and the information acquired at each time $t=t_0$ ms is stored in bin $B(10*INT(t_0/10))$, with information at annotation point P stored in bin B(0). Thus, information recorded at each interval is stored in respective bins B(0 ms), B(10 ms), B(20 ms), B(30 ms), etc., and the last bin B(i) contains the information recorded 10 ms prior to the annotation point P corresponding to the next heart beat. For some applications in which variation of the heart rate is expected, a characteristic heart rate is determined, and data taken during variations of the heart rate greater than about 2–10% from the characteristic heart rate (typically 5%) are excluded. In this manner, although the user typically is initially only presented with a map for annotation point P, system 20 can quickly calculate a map for essentially any point in the cardiac cycle when needed, as described hereinbelow.

Preferably, the position information at each time point in the cardiac cycle is acquired, and a geometric map based thereupon is generated when needed, using techniques described in the above-cited U.S. Pat. Nos. 6,226,542 and 6,301,496 to Reisfeld, European patent application EP 1 125 549 and corresponding U.S. patent application Ser. No. 09/506,766 to Ben-Haim et al., and/or co-pending U.S. patent application Ser. No. 09/598,862 to Govari, which are incorporated herein by reference, adapted for use with the techniques described herein. Preferably, but not necessarily, electrical signals from the electrodes are measured, in combination with the methods described hereinbelow, using techniques described in co-pending U.S. patent application Ser. No. 09/805,093, filed Mar. 13, 2001, entitled, "Apparatus and method for measuring a plurality of electrical signals from the body of a patient," which is assigned to the assignee of the present patent application and which is incorporated herein by reference.

In a preferred embodiment of the present invention, position information at each time point in the cardiac cycle is acquired by bringing tip 44 of catheter 30 into contact with wall 68 of chamber 66 at a first point 70 (FIG. 3A), or, alternatively, by bringing tip 44 into a vicinity of point 70 on wall 68. To the extent feasible, the shaft of catheter 30 is also positioned in contact with or near to the endocardium. Tip 44 is preferably maintained in contact with or near to point 70 throughout at least an entire cardiac cycle. Since the chamber wall at point 70 moves during the cardiac cycle as the chamber contracts and expands, tip 44 occupies a number of absolute coordinate positions during the cycle. Throughout the entire data collection process, position information is preferably continuously measured by position sensors 40 and 42. This position information is stored in bins B(i).

After the above position information is collected at each time point in the cardiac cycle when tip 44 is at or near point 70, the tip is advanced to a second point on the chamber surface. FIG. 3B shows tip 44 in contact with a second point 72 on chamber wall 68. FIG. 3B further shows point 70, and points 74, shown as asterisks, which represent locations occupied by the shaft of catheter 30 while tip 44 was at or near first point 70. Once again, the tip is preferably maintained in contact with wall 68 at or near contact point 72 throughout at least an entire cardiac cycle.

Tip 44 is preferably advanced over or in a vicinity of a plurality of points on the cardiac chamber surface. Preferably, the above-described information acquisition steps are effected at or near at least about five points on the cardiac chamber surface. More preferably, the information acquisition steps are effected at or in a vicinity of between about five and about fifteen points on the cardiac chamber surface. For each point, the catheter is preferably positioned so as to bring the shaft of catheter 30 into generally close proximity to or in contact with the endocardium.

It is noted that making contact between tip 44 and the various points on the endocardium is preferred in some applications so as to provide a protocol for user 22 that facilitates mapping of all or a desired portion of chamber 66. However, the procedure of mapping the chamber works irrespective of catheter contact with the endocardium, as long as the position sensors generate information to track the location of the catheter. Thus, even if tip 44 loses contact with the surface, or slides from one point to another during the cardiac cycle, the position data are typically utilized in generating a map.

The resultant position information acquired at each of the above-defined steps and stored in bins B(i) for each time interval $t_i$ in the cardiac cycle, provides the starting point for generating geometric maps of the heart chamber. Initially, a map of the chamber at annotation point P is preferably generated, using information stored in bin(0).

Typically, a tentative map of the chamber at annotation P is generated in real-time as the catheter is being moved around the chamber, as described above. The accuracy of the map increases as additional data are collected and analyzed. Optionally, the map is displayed in real-time on display 36 as it is being constructed. Preferably the map is three-dimensional, and can be rotated by user 22 to facilitate examination of the chamber.

In order to generate the map, position information is preferably obtained from position sensors 40 and 42. This information is used for all points in time, without regard to which electrodes, if any, are in contact with the chamber wall. Position information from sensor 40 adjacent distal tip 44 is used to determine the position of distal tip 44. Position information from sensor 40 and position information from sensor 42 (affixed near the proximal end of the array of shaft electrodes 46) are used together to determine the position of a large number of points on the catheter between the two position sensors. This determination is attained in a straight-forward manner, because for each combination of positions of sensors 40 and 42 relative to each other, measured in five or six dimensions, and for predetermined mechanical properties of the catheter, there is a least-energy shape in which the catheter is likely to be disposed. The shape for a given combination of sensor positions can be calculated using techniques known in the art, or, alternatively, empirically observed prior to a procedure, such as at the time of manufacture, and stored in a table in the processor. Because the catheter typically remains within the chamber for the duration of the data acquisition, the points at which the catheter is located, at any given point in the cardiac cycle, represent points where the endocardium is not located, and thus define the interior of the chamber. This information is used to construct a map, as follows.

An initial, generally arbitrary, closed three-dimensional curved surface (also referred to herein for brevity as a curve) is defined in a reconstruction space in the volume of the points determined to represent the location of the catheter. The closed curve is roughly adjusted to a shape which surrounds the points. Thereafter, a flexible matching procedure is preferably performed one or more times in order to bring the closed curve to accurately resemble the shape of the actual volume being reconstructed. The reconstruction typically rapidly increases in accuracy as the proximity of points on the catheter to the endocardium increases.

Typically, the initial closed three-dimensional curved surface comprises an ellipsoid, or any other simple closed curve. Alternatively, a non-closed curve may be used, for example, when it is desired to reconstruct a single wall rather than the entire volume.

In a preferred embodiment of the present invention, catheter 30 remains in chamber 66 after position information for the chamber has been acquired for the cardiac cycle at a plurality of points on or near wall 68, and, typically, after a map of the position information has been generated for annotation time point P and displayed on display 36. Preferably, using previously-acquired data (such as ECG data or anatomical information), catheter 30 is positioned near the site of an expected transient event on wall 68 of chamber 66. Position and electrical information is collected by the position sensors on catheter 30, and is preferably stored periodically in bins B(i). Additionally, electrodes 46 and 48 collect data representative of electrical activity in the vicinity of the electrodes, and these data are also stored.

If a transient event occurs and is detected by user 22, or by means of ECG and/or other monitoring data during this monitoring stage of the procedure, a determination is made of the point in the cardiac cycle, relative to the most recent annotation point P, at which the transient event commenced. The bin B(j) corresponding to the transient event is identified by selecting the time j recorded at or immediately prior to the determined point in the cardiac cycle at which the transient event commenced. For example, if the transient event commenced 432 ms after point P, then bin B(430 ms) corresponding to time j=430 ms is selected. The position information stored in bin B(j) is accessed by the processor in order to rapidly generate a map of chamber 66 at time j, based on data already acquired. This map therefore represents the geometry of chamber 66 at a reconstruction point in time j closely corresponding to the time point in the cardiac cycle when the transient event occurred. Optionally, this map is displayed on display 36.

Using the map so generated, the output of electrodes 46 and 48 recorded at the time of the transient event is analyzed by the processor in console 34 to determine which electrode was nearest to the site on wall 68 that initiated the transient event. This generates location information indicating the site of the transient event, which can be used for diagnostic, treatment, and/or other purposes. Optionally, the processor additionally determines which other electrodes were near the site of the transient event, and uses the data generated by these electrodes to generate additional information about the site of the transient event. In a preferred display mode, color coding is applied to the data recorded by the electrodes, such that, for example, red indicates an earliest activation time and purple indicates a latest activation time. The location of the transient event would in this case be indicated in red.

A preferred method for facilitating such an analysis from the acquired location and electrical information includes techniques described in the above-cited U.S. Pat. Nos. 6,226,542 and 6,301,496 to Reisfeld. Alternatively or additionally, techniques may be used which are described in the above-cited co-pending U.S. patent application Ser. No. 09/598,862 to Govari.

In a preferred embodiment of the present invention, in order to increase the quality of the electrical data, each position in the chamber that is measured by the shaft electrodes is measured by a set of shaft electrodes, preferably four shaft electrodes, situated near each other on the catheter. The electrodes of this set are preferably equally spaced about the catheter circumference in columns. Optionally, the location of the electrodes in each column is longitudinally offset relative to the location of the corresponding electrodes in adjacent columns. For each point in time, measurements from the electrodes of the set are compared. If there is a certain level of agreement among the electrodes, the measurements from the agreeing electrodes are averaged and used, and the measurements from the non-agreeing electrodes are discarded. Preferably, when the set contains four electrodes, three or four of the electrodes must agree for the measurements from these agreeing electrodes to be used. Agreement is preferably determined relative to narrowly-defined tolerance levels of variation in the magnitude and/or timing of the signals. Typically, a plurality of such sets are provided, each set at its own respective longitudinal position on the catheter. For each set, a vote requiring 3–1 or 4–0 agreement is typically utilized, in order to allow evaluation of the gathered data. Experiments have shown that although such strict criteria typically generate a large quantity of discarded data, the data that are maintained are of high quality, and accurately reflect the electrical activity of the heart at the indicated site.

Preferably, in order to generate additional information regarding the site of the transient event, catheter 30 is repositioned near the site of the transient event, preferably at a different orientation, for example, 90 degrees from its original orientation. To the extent possible, catheter 30 is preferably positioned at a location closer to the site of the transient event. Catheter 30 remains in this new position in expectation of the reoccurrence of a transient event at the same site. During this waiting time, position and electrical information continues to be generated by the position sensors and electrodes on catheter 30. Upon a reoccurrence of the transient event, additional information regarding the site of the transient event is generated, typically sufficient to accurately identify the location on the endocardium of the site, using the procedures described hereinabove. If appropriate, this repositioning and data collection step can be performed more than once.

In a preferred embodiment of the present invention, after the data collection described hereinabove is concluded and the location of the site of the transient event at the reconstruction point in time j has been determined, the map of chamber 66 at the reconstruction point in time j is displayed on display 36, showing the site of the transient event. Using this map, tip 44 of catheter 30 is positioned at the site of the transient event. A suitable diagnostic procedure (e.g., pace mapping) or therapeutic procedure (e.g., ablation) is then typically performed.

In a preferred embodiment, a catheter tip icon is displayed or superimposed on the generated transient event map. The tip icon is displayed at a time in the cardiac cycle corresponding to the transient event (e.g., at 430 ms with respect to the sinus rhythm cycle). This can be done because of the continuous recording of tip location throughout the cardiac cycle (e.g., every 10 ms). This in turn facilitates navigation during sinus rhythm on the map representing the anatomy of the heart and its electrical activation as recorded at the time in the cardiac cycle of the transient event.

It is noted that at this point in the procedure, the location of the transient event is not yet known with respect to the map representing the heart at the annotation point (e.g., end-diastole), and, for some applications, it is preferable to be able to identify the location of the transient event on a map showing the heart at the annotation point. To facilitate such an identification, while the catheter is held in this position, the map at annotation point P is displayed on display 36, and the location of the tip on the map is displayed. Since the tip of the catheter is on the site of the transient event, the site of the transient event is thereby located in the reference frame of the electrical map representing the heart at annotation point P in the cardiac cycle. Preferably, with this absolute knowledge of the site of the transient event in the reference frame of annotation point P, diagnosis, additional data collection, and/or treatment (for example, ablation) is performed.

Figure 4:
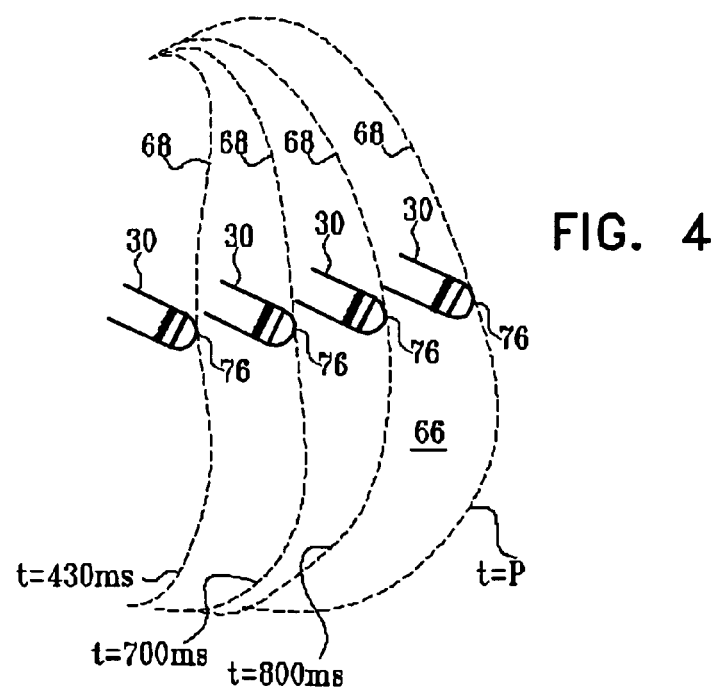
FIG. 4 is a schematic, sectional illustration of a heart at several points in the cardiac cycle, showing the distal end of the catheter positioned at a site of a transient event, in accordance with a preferred embodiment of the present invention.

Reference is now made to FIG. 4, which is a schematic, sectional illustration of heart 24 at several points in the cardiac cycle, showing the distal end of catheter 30 positioned at a site 76 determined to be the site of a transient event, in accordance with a preferred embodiment of the present invention. Typically, after the data collection described hereinabove is concluded and the location of the site of the transient event at the reconstruction point in time j has been determined, the map of chamber 66 at the reconstruction point in time j is displayed on display 36. Using this map, tip 44 of catheter 30 is positioned at site 76 of the transient event at the reconstruction point in time j, shown, for illustrative purposes, as t=430 ms in FIG. 4. At this point, a diagnostic or therapeutic procedure may be performed.

Alternatively, the tip may be physically held in contact with the endocardium on the site of the transient event on wall 68 at least through the next occurrence of annotation point P in the cardiac cycle, during which time position information for the tip is acquired. In FIG. 4, for illustrative purposes, the tip is shown passing through time points t=700 ms and t=800 ms, before arriving at the next cardiac cycle's annotation point P at end-diastole (which is assumed, for example, to occur at t=900 ms, corresponding to t=0 ms). Using the determined position at annotation point P, the location of the transient event on the map of wall 68 at annotation point P is determined, and the diagnostic or therapeutic procedure may be performed at the location of the transient event using the displayed map at the annotation point as a guide.

In a preferred embodiment of the present invention, electrical data generated by the electrodes are analyzed depending on the distance of the respective electrodes from the chamber wall at the time of measurement. A near-field function is preferably used to analyze data generated by an electrode that is within a threshold distance from the chamber wall (a "near-field electrode"). The threshold distance is preferably but not necessarily between about 6 and 10 mm, and is typically approximately 8 mm. Data generated by "far-field electrodes," i.e., those that are more than the threshold distance from the chamber wall, are typically not analyzed (unless a determination of the distance is subsequently adjusted). Electrical characteristics measured by the electrodes are preferably selected from local voltage, local impedance, local conduction velocity or local activation time. It is noted that use of the technique of providing such a threshold distance is not limited to use in transient event mapping applications, but is useful in a range of applications where fast cardiac electrical mapping is desirable.

Since in some fast cardiac electrical mapping applications the electrical aspect of the map is preferably generated as the geometric aspect is being generated, the geometric map available upon which to build the electrical map is initially only a rough approximation of the chamber geometry. For each electrode, including both tip and shaft electrodes, a determination as to whether it is currently a near-field or far-field electrode is made based on the geometric map then available. The decision of whether to utilize a near-field function or to withhold analyzing the electrode's generated data is made responsive to the current approximation of the chamber geometry. As the geometry of the chamber is refined as additional position data become available, the near- or far-field determinations made thus far are preferably continually reviewed and corrected, if necessary.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for performing a medical procedure, comprising:

providing a catheter having at least one position sensor for generating or receiving signals for use in determining position information of a portion of the catheter in a heart of a subject;

recording geometric information at a plurality of time points in a plurality of cardiac cycles of the heart of the subject using the at least one position sensor of the catheter;

subsequently detecting a transient event produced at a location on the heart during a cardiac cycle;

identifying a time of occurrence of the transient event in the cardiac cycle during which the transient event occurred; and displaying a map of the heart responsive to the identified time of occurrence and the geometric information recorded at a time point in the cardiac cycle that corresponds to the time of occurrence of the transient event.

\* \* \* \* \*